United States Patent [19]

Dean et al.

[11] Patent Number: 5,989,519
[45] Date of Patent: *Nov. 23, 1999

[54] TECHNETIUM-99M LABELED PEPTIDES FOR IMAGING INFLAMMATION

[75] Inventors: Richard T. Dean, Bedford, N.H.; Robert S. Lees, Brookline, Mass.; Scott Buttram, Derry; John Lister-James, Bedford, both of N.H.

[73] Assignee: Diatide, Inc., Londonderry, N.H.

[*] Notice: This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 08/290,853

[22] PCT Filed: Mar. 12, 1993

[86] PCT No.: PCT/US93/02320

§ 371 Date: Oct. 11, 1994

§ 102(e) Date: Oct. 11, 1994

[87] PCT Pub. No.: WO93/17719

PCT Pub. Date: Sep. 16, 1993

Related U.S. Application Data

[63] Continuation-in-part of application No. 07/851,074, Mar. 12, 1992, abandoned, and application No. 08/253,678, Jun. 3, 1994.

[51] Int. Cl.$^6$ .................... A61K 51/00; A61M 36/14
[52] U.S. Cl. ............... 424/1.69; 424/1.11; 424/1.65; 534/14; 530/300
[58] Field of Search .................. 424/1.11, 1.37, 424/1.49, 1.53, 1.65, 1.69, 9.1; 530/300, 324–330, 333, 334, 338; 534/10–16; 206/569

[56] References Cited

U.S. PATENT DOCUMENTS

| | | | |
|---|---|---|---|
| 4,986,979 | 1/1991 | Morgan, Jr. et al. | 424/1.11 |
| 4,988,496 | 1/1991 | Srinivasan et al. | 424/1.11 |
| 5,277,892 | 1/1994 | Rhodes | 424/1.69 |
| 5,376,356 | 12/1994 | Morgan, Jr. | 424/1.11 |
| 5,443,815 | 8/1995 | Dean et al. | 424/1.69 |
| 5,508,020 | 4/1996 | Dean et al. | 424/1.69 |
| 5,720,934 | 2/1998 | Dean et al. | 424/1.69 |
| 5,759,515 | 6/1998 | Rhodes et al. | 424/1.69 |

FOREIGN PATENT DOCUMENTS

| | | |
|---|---|---|
| 0174853 | 3/1985 | European Pat. Off. . |
| 0398143 | 11/1990 | European Pat. Off. . |
| 0403243 | 12/1990 | European Pat. Off. . |
| 0453082 | 10/1991 | European Pat. Off. . |
| 0649857 | 4/1995 | European Pat. Off. . |
| 8910759 | 11/1989 | WIPO . |
| 9010463 | 9/1990 | WIPO . |
| 9116919 | 11/1991 | WIPO . |
| 9213572 | 8/1992 | WIPO . |
| 9317719 | 9/1993 | WIPO . |
| 9321962 | 11/1993 | WIPO . |
| 9325244 | 12/1993 | WIPO . |
| 9419024 | 9/1994 | WIPO . |
| 9423758 | 10/1994 | WIPO . |
| 9428942 | 12/1994 | WIPO . |
| 9529708 | 11/1995 | WIPO . |
| 9533496 | 12/1995 | WIPO . |
| 9533497 | 12/1995 | WIPO . |
| 9533498 | 12/1995 | WIPO . |

OTHER PUBLICATIONS

Moyer et al (1996), J. Nucl. Med, vol. 37, No. 4, pp. 673–679, "Technetium–99m White Blood Cell Specific Imaging Agent Developed from Platelet Factor & to Detect Infection."

Zoghbi et al., 1981, "Selective cell labeling: a potential radioactive agent for labeling human neutrophils", *J. Nucl. Med.* 22: 32 (Abst).

Jiang et al., 1982, "Localization of abscess with an iodinated synthetic chemotactic peptide", *Nuklearmedizin* 21: 110–113.

Ebright et al., 1982, "The gallium scan: Problems and misuse in examination of patients with suspected infection", *Arch. Int. Med.* 142: 246–254.

Brenner et al., 1984, "Synthesis and Characterization of a Series of Isomeric Oxotechnetium (V) Diamido Dithiolates", *Inorg. Chem.* 23: 3793–3797.

Epps et al., 1987, "Brain Imaging Agents: Synthesis and Characterization of (N–Piperidinylethyl) Hexamethyl Diaminoditholate Oxo Technetium (V) Complexes" *Appl. Radiat. Isot.* 38: 661–664.

Wilkinson, 1988, "Chemotactic factors: an overview", *Meth. Enzymol.* 162: 127–132.

Tam, 1968, "Synthetic peptide vaccine design: Synthesis and properties of a high–density multiple antigenic peptide system", *Proc. Natl. Acad. Sci. USA* 85: 5409–5413.

Fritzberg et al., 1988, "Specific and stable labeling of antibodies with technetium–99m with a diamide dithiolate chelating agent", *Proc. Natl. Acad. Sci. USA* 85: 4025–4029.

Harlow & Lane, 1988, "Chapter: Immunizations", in *The Antibodies: A Laboratory Manual*, Cold Spring Harbor Laboratory Press, Cold Spring Harbor, N.Y., pp. 53–137.

Vorne et al., 1989, "Technetium–99m HM–PAO–labeled leukocytes in detection of inflammatory lesions: Comparison with gallium–67 citrate", *J. Nucl. Med.* 30: 1332–1336.

LaMuraglia et al., 1989, "Utility of the indium 111–labeled human immunoglobulin G scan for the detection of focal vascular graft infection", *J. Vasc. Surg.* 10: 20–28.

(List continued on next page.)

*Primary Examiner*—Jose' G. Dees
*Assistant Examiner*—Dameron Jones
*Attorney, Agent, or Firm*—Patricia A. McDaniels; Kevin E. Noonan

[57] ABSTRACT

This invention relates to radiolabeled peptides and methods for producing such peptides. Specifically, the invention relates to technetium-99m (Tc-99m) labeled leukocyte-binding peptides, methods and kits for making such peptides, and methods for using such peptides to image sites of infection and inflammation in a mammalian body.

31 Claims, 1 Drawing Sheet

OTHER PUBLICATIONS

Lind et al., 1990, "Immunoscintigraphy of inflammatory processes with a technetium–99m–labeled monoclonal anti-granulocyte antibody (MAb BW 250/183)", *J. Nucl. Med. 31:* 417–473.

Baidoo & Lever, 1990, "Synthesis of a Diaminedithiol Bifunctional Chelating Agent for Incorporation of Technetium–99m into Biomolecules", *Bioconjugate Chem. 1:* 132–137.

Bryson et al., 1990, "Protecting Groups in the Preparation of Thiolate Complexes of Technetium", *Inorganic Chem. 29:* 2948–2951.

Fischman et al., 1991, "Imaging focal sites of bacterial infection in rats with indium–111–labeled chemotactic peptide analogs", *J. Nucl. Med. 32:* 482–491.

Peters, 1992, "Imaging Inflammation: Current role of labeled autologous leukocytes", *J. Nucl. Med. 33:* 65–67.

Najifi et al., 1992, "The Evaluation of $^{186}$Re–labeled Antibodies Using $N_2S_4$ Chelate In Vitro and in Vivo Using Tumor–bearing Nude Mice", *Nucl. Med. Biol. 19:* 205–212.

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
       (A) LENGTH: 6 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 4..6
       (D) OTHER INFORMATION: /label= Protected-Cys
           /note= "The thiol of the carboxyl terminal cysteine
           and of the cysteine at position 4 is a acetamidomethyl
           group"

(ix) FEATURE:
       (A) NAME/KEY: Modified-site
       (B) LOCATION: 1
       (D) OTHER INFORMATION: /label= formyl-Met
           /note= "The amino terminus is linked to a formyl
           group"

(xi) SEQUENCE DESCRIPTION: SEQ ID NO:1:

Met Leu Phe Cys Gly Cys
   1               5

(2) INFORMATION FOR SEQ ID NO:2:

(i) SEQUENCE CHARACTERISTICS:
       (A) LENGTH: 21 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1..3
       (D) OTHER INFORMATION: /label= Modified-Cys
           /note= "The thiol group of each cysteine is
           protected by an acetamidomethyl group."

(xi) SEQUENCE DESCRIPTION: SEQ ID NO:2:

Cys Gly Cys Val Gly Val Ala Pro Gly Val Gly Val Ala Pro Gly Val
   1               5                   10                  15

Gly Val Ala Pro Gly
               20

(2) INFORMATION FOR SEQ ID NO:3:

(i) SEQUENCE CHARACTERISTICS:
       (A) LENGTH: 7 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 5..7
       (D) OTHER INFORMATION: /label= Protected-Cys
           /note= "The thiol of the carboxyl terminal cysteine
           and of the cysteine at position 4 is a acetamidomethyl
           group"

```
    (ix) FEATURE:
         (A) NAME/KEY: Modified-site
         (B) LOCATION: 1
         (D) OTHER INFORMATION: /label= formyl-Met
             /note= "The amino terminus is linked to a formyl
             group"

(xi) SEQUENCE DESCRIPTION: SEQ ID NO:3:

Met Ile Leu Phe Cys Gly Cys
    1               5

(2) INFORMATION FOR SEQ ID NO:4:

(i) SEQUENCE CHARACTERISTICS:
         (A) LENGTH: 7 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 1..3
         (D) OTHER INFORMATION: /label= Modified-Cys
             /note= "The thiol group of each cysteine is
             protected by an acetamidomethyl group."

(xi) SEQUENCE DESCRIPTION: SEQ ID NO:4:

Cys Gly Cys Thr Lys Pro Arg
    1               5

(2) INFORMATION FOR SEQ ID NO:5:

(i) SEQUENCE CHARACTERISTICS:
         (A) LENGTH: 5 amino acids
         (B) TYPE: amino acid
         (D) TOPOLOGY: linear (ii) MOLECULE TYPE: peptide (ix) FEATURE:
         (A) NAME/KEY: Modified-site
         (B) LOCATION: 3..5
         (D) OTHER INFORMATION: /label= Modified-Cys
             /note= "The thiol group of the cysteine is
             protected with an acetamidomethyl group; the carboxyl
             terminal glycine is linked to a Pica group."

(ix) FEATURE:
         (A) NAME/KEY: Modified-site
         (B) LOCATION: 1
         (D) OTHER INFORMATION: /label= formyl-Met
             /note= "The amino terminus is linked to a formyl
             group"

(xi) SEQUENCE DESCRIPTION: SEQ ID NO:5:

Met Leu Phe Cys Gly
    1               5

(2) INFORMATION FOR SEQ ID NO:6:

(i) SEQUENCE CHARACTERISTICS:
         (A) LENGTH: 9 amino acids
         (B) TYPE: amino acid
         (D) TOPOLOGY: linear (ii) MOLECULE TYPE: peptide (ix) FEATURE:
         (A) NAME/KEY: Peptide
         (B) LOCATION: 1..4
         (D) OTHER INFORMATION: /label= Norleucine
             /note= "Each of the Xaa residues is norleucine; the
             amino terminal norleucine is formylated."
```

(ix) FEATURE:
         (A) NAME/KEY: Modified-site
         (B) LOCATION: 7..9
         (D) OTHER INFORMATION: /label= Modified-Cys
             /note= "The thiol group of the cysteine is
             protected with an acetamidomethyl group."

(xi) SEQUENCE DESCRIPTION: SEQ ID NO:6:

Xaa Leu Phe Xaa Tyr Lys Cys Gly Cys
    1               5

(2) INFORMATION FOR SEQ ID NO:7:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
         (A) NAME/KEY: Modified-site
         (B) LOCATION: 1..3
         (D) OTHER INFORMATION: /label= Picolinoyl
             /note= "The amino terminal residue is
             pyridine-2-carbonyl; the thiol of the cysteine is
             protected by an acetamidomethyl group."

(ix) FEATURE:
         (A) NAME/KEY: Modified-site
         (B) LOCATION: 21
         (D) OTHER INFORMATION: /label= Amide
             /note= "The carboxyl terminus is modified to an
             amide"

(xi) SEQUENCE DESCRIPTION: SEQ ID NO:7:

Xaa Gly Cys Val Gly Val Ala Pro Gly Val Gly Val Ala Pro Gly Val
    1               5                   10                  15

Gly Val Ala Pro Gly
                20

(2) INFORMATION FOR SEQ ID NO:8:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (ix) FEATURE:
         (A) NAME/KEY: Modified-site
         (B) LOCATION: 1..3
         (D) OTHER INFORMATION: /label= Picolinoyl
             /note= "The amino terminal residue is
             pyridine-2-carbonyl; the thiol of the cysteine is
             protected by an acetamidomethyl group."

(ix) FEATURE:
         (A) NAME/KEY: Modified-site
         (B) LOCATION: 23
         (D) OTHER INFORMATION: /label= Amide
             /note= "The carboxyl terminus is modified to an
             amide"

(xi) SEQUENCE DESCRIPTION: SEQ ID NO:8:

Xaa Gly Cys Val Pro Gly Val Gly Val Pro Gly Val Gly Val Pro Gly
    1               5                   10                  15

Val Gly Val Pro Gly Val Gly
                20

(2) INFORMATION FOR SEQ ID NO:9:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= Picolinoyl
            /note= "The amino terminal residue is
            pyridine-2-carbonyl; the thiol of the cysteine is
            protected by an acetamidomethyl group."

(xi) SEQUENCE DESCRIPTION: SEQ ID NO:9:

Gly Cys Pro Leu Tyr Lys Lys Ile Ile Lys Lys Leu Leu Glu Ser
1               5                   10                  15

(2) INFORMATION FOR SEQ ID NO:10:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= Modified-Cys
            /note= "The thiol group of the cysteine is
            protected with an acetamidomethyl group."

(xi) SEQUENCE DESCRIPTION: SEQ ID NO:10:

Cys Gly Cys Gly Gly Pro Leu Tyr Lys Lys Ile Ile Lys Lys Leu Leu
1               5                   10                  15

Glu Ser (2) INFORMATION FOR SEQ ID NO:11:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 15..17
        (D) OTHER INFORMATION: /label= Modified-Cys
            /note= "The thiol group of each cysteine is
            protected by an acetamidomethyl group."

(ix) FEATURE:
        (A) NAME/KEY: Peptide
        (B) LOCATION: 1
        (D) OTHER INFORMATION: /label= pyro-Glu
            /note= "The Xaa residue is pyro-glutamic acid."

(ix) FEATURE:
        (A) NAME/KEY: Modified-site
        (B) LOCATION: 17
        (D) OTHER INFORMATION: /label= Amide
            /note= "The carboxyl terminus is modified to an
            amide"

(xi) SEQUENCE DESCRIPTION: SEQ ID NO:11:

Xaa Gly Val Asn Asp Asn Glu Glu Gly Phe Phe Ser Ala Arg Cys Gly
1               5                   10                  15

Cys (2) INFORMATION FOR SEQ ID NO:12:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 24..26
        (D) OTHER INFORMATION: /label= Protected-Cys
            /note= "The thiol of the carboxyl terminal cysteine
            and of the cysteine at position 24 is a acetamidomethyl
            group"

(ix) FEATURE:
        (A) NAME/KEY: Modified-site
        (B) LOCATION: 26
        (D) OTHER INFORMATION: /label= Amide
            /note= "The carboxyl terminus is modified to an
            amide"

(xi) SEQUENCE DESCRIPTION: SEQ ID NO:12:

```
Val Pro Gly Val Gly Val Pro Gly Val Gly Val Pro Gly Val Gly Val
1               5                   10                  15
Pro Gly Val Gly Gly Gly Gly Cys Gly Cys
            20                  25
```

(2) INFORMATION FOR SEQ ID NO:13:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 22..24
        (D) OTHER INFORMATION: /label= Protected-Cys
            /note= "The thiol of the carboxyl terminal cysteine
            and of the cysteine at position 22 is a acetamidomethyl
            group"

(ix) FEATURE:
        (A) NAME/KEY: Modified-site
        (B) LOCATION: 24
        (D) OTHER INFORMATION: /label= Amide
            /note= "The carboxyl terminus is modified to an
            amide"

(xi) SEQUENCE DESCRIPTION: SEQ ID NO:13:

```
Val Gly Val Ala Pro Gly Val Gly Val Ala Pro Gly Val Gly Val Ala
1               5                   10                  15
Pro Gly Gly Gly Gly Cys Gly Cys
            20
```

(2) INFORMATION FOR SEQ ID NO:14:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (ix) FEATURE:

(A) NAME/KEY: Modified-site
              (B) LOCATION: 1..3
              (D) OTHER INFORMATION: /label= Protected-Cys
                  /note= "The thiol of each cysteine is protected
                  by an acetamidomethyl group."

(ix) FEATURE:
              (A) NAME/KEY: Modified-site
              (B) LOCATION: 1..3
              (D) OTHER INFORMATION: /label= acetyl-Cys
                  /note= "The amino terminal residue is
                  linked to an acetyl group."

(ix) FEATURE:
              (A) NAME/KEY: Modified-site
              (B) LOCATION: 26
              (D) OTHER INFORMATION: /label= Amide
                  /note= "The carboxyl terminus is modified to an
                  amide"

(xi) SEQUENCE DESCRIPTION: SEQ ID NO:14:

Cys Gly Cys Gly Gly Gly Val Pro Gly Val Gly Val Pro Gly Val Gly
   1               5                  10                  15

Val Pro Gly Val Gly Val Pro Gly Val Gly
               20                  25

(2) INFORMATION FOR SEQ ID NO:15:

(i) SEQUENCE CHARACTERISTICS:
              (A) LENGTH: 24 amino acids
              (B) TYPE: amino acid
              (D) TOPOLOGY: linear (ii) MOLECULE TYPE: peptide (ix) FEATURE:
              (A) NAME/KEY: Modified-site
              (B) LOCATION: 1..3
              (D) OTHER INFORMATION: /label= Protected-Cys
                  /note= "The thiol of each cysteine is protected
                  by an acetamidomethyl group."

(ix) FEATURE:
              (A) NAME/KEY: Modified-site
              (B) LOCATION: 1..3
              (D) OTHER INFORMATION: /label= acetyl-Cys
                  /note= "The amino terminal residue is
                  linked to an acetyl group."

(ix) FEATURE:
              (A) NAME/KEY: Peptide
              (B) LOCATION: 4
              (D) OTHER INFORMATION: /label= Aca
                  /note= "The Xaa residue is epsilon amino caproic
                  acid."

(ix) FEATURE:
              (A) NAME/KEY: Modified-site
              (B) LOCATION: 24
              (D) OTHER INFORMATION: /label= Amide
                  /note= "The carboxyl terminus is modified to an
                  amide"

(xi) SEQUENCE DESCRIPTION: SEQ ID NO:15:

Cys Gly Cys Xaa Val Pro Gly Val Gly Val Pro Gly Val Gly Val Pro
   1               5                  10                  15

Gly Val Gly Val Pro Gly Val Gly
               20

(2) INFORMATION FOR SEQ ID NO:16:

(i) SEQUENCE CHARACTERISTICS:
              (A) LENGTH: 17 amino acids
              (B) TYPE: amino acid

```
        (D) TOPOLOGY: linear (ii) MOLECULE TYPE: peptide (ix) FEATURE:
         (A) NAME/KEY: Modified-site
         (B) LOCATION: 1..3
         (D) OTHER INFORMATION: /label= acetyl-Cys
             /note= "The amino terminal residue is
             linked to an acetyl group."

(xi) SEQUENCE DESCRIPTION: SEQ ID NO:16:

Cys Gly Gly Gly Pro Leu Tyr Lys Lys Ile Ile Lys Lys Leu Leu Glu
    1               5                  10                  15

Ser (2) INFORMATION FOR SEQ ID NO:17:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (ix) FEATURE:
         (A) NAME/KEY: Modified-site
         (B) LOCATION: 1..3
         (D) OTHER INFORMATION: /label= Picolinoyl
             /note= "The amino terminal residue is
             pyridine-2-carbonyl."

(ix) FEATURE:
         (A) NAME/KEY: Modified-site
         (B) LOCATION: 21
         (D) OTHER INFORMATION: /label= Amide
             /note= "The carboxyl terminus is modified to an
             amide"

(xi) SEQUENCE DESCRIPTION: SEQ ID NO:17:

Xaa Gly Cys Val Gly Val Ala Pro Gly Val Gly Val Ala Pro Gly Val
    1               5                  10                  15

Gly Val Ala Pro Gly
                20

(2) INFORMATION FOR SEQ ID NO:18:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (ix) FEATURE:
         (A) NAME/KEY: Peptide
         (B) LOCATION: 1
         (D) OTHER INFORMATION: /label= pyro-Glu
             /note= "The Xaa residue is pyro-glutamic acid."

(ix) FEATURE:
         (A) NAME/KEY: Modified-site
         (B) LOCATION: 17
         (D) OTHER INFORMATION: /label= Amide
             /note= "The carboxyl terminus is modified to an
             amide"

(xi) SEQUENCE DESCRIPTION: SEQ ID NO:18:

Xaa Gly Val Asn Asp Asn Glu Glu Gly Phe Phe Ser Ala Arg Gly Gly
    1               5                  10                  15

Cys
```

(2) INFORMATION FOR SEQ ID NO:19:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 21..23
        (D) OTHER INFORMATION: /label= Protected-Cys
            /note= "The thiol of the carboxyl terminal cysteine
            and of the cysteine at position 21 is a acetamidomethyl
            group"

(ix) FEATURE:
        (A) NAME/KEY: Modified-site
        (B) LOCATION: 1..3
        (D) OTHER INFORMATION: /label= acetyl-Cys
            /note= "The amino terminal residue is
            linked to an acetyl group."

(ix) FEATURE:
        (A) NAME/KEY: Modified-site
        (B) LOCATION: 23
        (D) OTHER INFORMATION: /label= Amide
            /note= "The carboxyl terminus is modified to an
            amide"

(xi) SEQUENCE DESCRIPTION: SEQ ID NO:19:

```
Leu Lys Lys Leu Leu Lys Lys Leu Leu Lys Lys Leu Leu Lys Lys Leu
1               5                   10                  15

Leu Lys Lys Leu Cys Gly Cys
            20
```

(2) INFORMATION FOR SEQ ID NO:20:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= BAT
            /note= "The amino terminal residue is
            linked to a BAT radiolabel binding moiety."

(xi) SEQUENCE DESCRIPTION: SEQ ID NO:20:

```
Gly Gly Pro Leu Tyr Lys Lys Ile Ile Lys Lys Leu Leu Glu Ser
1               5                   10                  15
```

(2) INFORMATION FOR SEQ ID NO:21:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2..4
        (D) OTHER INFORMATION: /label= Modified-Lys
            /note= "The carboxyl terminal lysine is linked
            to a BAT radiolabel binding moiety."

(ix) FEATURE:

(A) NAME/KEY: Modified-site
            (B) LOCATION: 4
            (D) OTHER INFORMATION: /label= Amide
                /note= "The carboxyl terminus is modified to an
                amide"

(xi) SEQUENCE DESCRIPTION: SEQ ID NO:21:

Met Leu Phe Lys
    1

(2) INFORMATION FOR SEQ ID NO:22:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 2..4
        (D) OTHER INFORMATION: /label= Modified-Lys
            /note= "The carboxyl terminal lysine is linked
            to a BAT radiolabel binding moiety."

(xi) SEQUENCE DESCRIPTION: SEQ ID NO:22:

Met Leu Phe Lys
    1

(2) INFORMATION FOR SEQ ID NO:23:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= BAT
            /note= "The amino terminal residue is
            linked to a BAT radiolabel binding moiety."

(ix) FEATURE:
        (A) NAME/KEY: Modified-site
        (B) LOCATION: 20
        (D) OTHER INFORMATION: /label= Amide
            /note= "The carboxyl terminus is modified to an
            amide"

(xi) SEQUENCE DESCRIPTION: SEQ ID NO:23:

Val Pro Gly Val Gly Val Pro Gly Val Gly Val Pro Gly Val Gly Val
    1               5                   10                  15

Pro Gly Val Gly
              20

(2) INFORMATION FOR SEQ ID NO:24:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 3..5
        (D) OTHER INFORMATION: /label= Modified-Lys
            /note= "The lysine at position 5 is linked to -continued

```
            a BAT radiolabel binding moiety."

(ix) FEATURE:
          (A) NAME/KEY: Modified-site
          (B) LOCATION: 9
          (D) OTHER INFORMATION: /label= Amide
              /note= "The carboxyl terminus is modified to an
              amide"

(xi) SEQUENCE DESCRIPTION: SEQ ID NO:24:

Met Leu Phe Lys Lys Lys Lys Lys
    1               5

(2) INFORMATION FOR SEQ ID NO:25:

(i) SEQUENCE CHARACTERISTICS:
          (A) LENGTH: 8 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 3..5
          (D) OTHER INFORMATION: /label= Modified-Lys
              /note= "The lysine at position 5 is linked to
              a BAT radiolabel binding moiety."

(ix) FEATURE:
          (A) NAME/KEY: Modified-site
          (B) LOCATION: 8
          (D) OTHER INFORMATION: /label= Amide
              /note= "The carboxyl terminus is modified to an
              amide"

(xi) SEQUENCE DESCRIPTION: SEQ ID NO:25:

Met Leu Phe Lys Gly Ser Gly Ser
    1               5

(2) INFORMATION FOR SEQ ID NO:26:

(i) SEQUENCE CHARACTERISTICS:
          (A) LENGTH: 5 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 2..4
          (D) OTHER INFORMATION: /label= Modified-Lys
              /note= "The lysine residue is linked to a BAT
              radiolabel binding moiety."

(xi) SEQUENCE DESCRIPTION: SEQ ID NO:26:

Met Leu Phe Lys Glu
    1               5

(2) INFORMATION FOR SEQ ID NO:27:

(i) SEQUENCE CHARACTERISTICS:
          (A) LENGTH: 7 amino acids
          (B) TYPE: amino acid
          (D) TOPOLOGY: linear (ii) MOLECULE TYPE: peptide (ix) FEATURE:
          (A) NAME/KEY: Modified-site
          (B) LOCATION: 2..4
          (D) OTHER INFORMATION: /label= Modified-Lys
              /note= "The lysine residue is linked to a BAT
``` radiolabel binding moiety."

(xi) SEQUENCE DESCRIPTION: SEQ ID NO:27:

Met Leu Phe Lys Glu Gly Glu
1               5

(2) INFORMATION FOR SEQ ID NO:28:

(i) SEQUENCE CHARACTERISTICS:
    (A) LENGTH: 18 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1..3
    (D) OTHER INFORMATION: /label= BAT
        /note= "The amino terminal residue is
        linked to a BAT radiolabel binding moiety."

(ix) FEATURE:
    (A) NAME/KEY: Modified-site
    (B) LOCATION: 18
    (D) OTHER INFORMATION: /label= Amide
        /note= "The carboxyl terminus is modified to an
        amide"

(xi) SEQUENCE DESCRIPTION: SEQ ID NO:28:

Val Gly Val Ala Pro Gly Val Gly Val Ala Pro Gly Val Gly Val Ala
1               5                   10                  15

Pro Gly (2) INFORMATION FOR SEQ ID NO:29:

(i) SEQUENCE CHARACTERISTICS:
    (A) LENGTH: 16 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1..3
    (D) OTHER INFORMATION: /label= Modified-Cys
        /note= "The thiol group of the cysteine is
        protected with an acetamidomethyl group."

(ix) FEATURE:
    (A) NAME/KEY: Modified-site
    (B) LOCATION: 1
    (D) OTHER INFORMATION: /label= DTPA
        /note= "The amino terminus is linked to a DTPA
        group"

(xi) SEQUENCE DESCRIPTION: SEQ ID NO:29:

Cys Gly Cys Pro Leu Tyr Lys Lys Ile Ile Lys Lys Leu Leu Glu Ser
1               5                   10                  15

(2) INFORMATION FOR SEQ ID NO:30:

(i) SEQUENCE CHARACTERISTICS:
    (A) LENGTH: 18 amino acids
    (B) TYPE: amino acid
    (D) TOPOLOGY: linear (ii) MOLECULE TYPE: peptide (ix) FEATURE:
    (A) NAME/KEY: Modified-site
    (B) LOCATION: 1

(D) OTHER INFORMATION: /label= BAT
                /note= "The amino terminus is linked to a BAT
                radiolabel binding moiety."

(xi) SEQUENCE DESCRIPTION: SEQ ID NO:30:

Lys Lys Leu Leu Lys Lys Leu Tyr Lys Lys Ile Ile Lys Lys Leu Leu
    1               5                   10                  15

Glu Ser (2) INFORMATION FOR SEQ ID NO:31:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 4..6
        (D) OTHER INFORMATION: /label= Modified-Cys
            /note= "The thiol group of the cysteine is
            protected with an acetamidomethyl group."

(ix) FEATURE:
        (A) NAME/KEY: Modified-site
        (B) LOCATION: 1
        (D) OTHER INFORMATION: /label= acetyl
            /note= "The amino terminus is linked to an acetyl
            group"

(xi) SEQUENCE DESCRIPTION: SEQ ID NO:31:

Cys Lys Lys Cys Gly Cys Pro Leu Tyr Lys Lys Ile Ile Lys Lys Leu
    1               5                   10                  15

Leu Glu Ser (2) INFORMATION FOR SEQ ID NO:32:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 4..6
        (D) OTHER INFORMATION: /label= Picolinoyl
            /note= "The thiol of the carboxyl terminal cysteine
            is protected by a 4-methoxybenzyl group; Xaa is pyridine-
            2-carbonyl.

(ix) FEATURE:
        (A) NAME/KEY: Modified-site
        (B) LOCATION: 3..4
        (D) OTHER INFORMATION: /label= Linker
            /note= "The carboxyl terminus of the phenylalanine
            residue and the amino terminua of the pyridine-2-carbonyl
            residue are linked via a NH(CH2CH2O)2CH2CH2NH linker."

(ix) FEATURE:
        (A) NAME/KEY: Modified-site
        (B) LOCATION: 1
        (D) OTHER INFORMATION: /label= formyl-Met
            /note= "The amino terminus is linked to a formyl
            group"

(xi) SEQUENCE DESCRIPTION: SEQ ID NO:32:

Met Leu Phe Xaa Gly Cys
    1               5

(2) INFORMATION FOR SEQ ID NO:33:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= BAT
            /note= "The amino terminus is linked to a BAT
            radiolabel binding moiety."

(ix) FEATURE:
        (A) NAME/KEY: Modified-site
        (B) LOCATION: 28
        (D) OTHER INFORMATION: /label= Amide
            /note= "The carboxyl terminus is modified to an
            amide"

(xi) SEQUENCE DESCRIPTION: SEQ ID NO:33:

Gly His Arg Pro Leu Asp Lys Lys Arg Glu Glu Ala Pro Ser Leu Arg
    1               5                   10                  15

Pro Ala Pro Pro Pro Ile Ser Gly Gly Gly Tyr Arg
                20                  25

(2) INFORMATION FOR SEQ ID NO:34:

(i) SEQUENCE CHARACTERISTICS:
        (A) LENGTH: 23 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 6..8
        (D) OTHER INFORMATION: /label= Modified-Cys
            /note= "The thiol group of the cysteine is
            protected with an acetamidomethyl group."

(ix) FEATURE:
        (A) NAME/KEY: Modified-site
        (B) LOCATION: 1
        (D) OTHER INFORMATION: /label= acetyl
            /note= "The amino terminus is linked to an acetyl
            group"

(xi) SEQUENCE DESCRIPTION: SEQ ID NO:34:

Lys Lys Lys Lys Lys Cys Gly Cys Gly Gly Pro Leu Tyr Lys Lys Ile
    1               5                   10                  15

Ile Lys Lys Leu Leu Glu Ser
                20

(2) INFORMATION FOR SEQ ID NO:35:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= Picolinoyl
            /note= "The amino terminal residue is
            pyridine-2-carbonyl; the thiol of the cysteine is -continued

```
        protected by an acetamidomethyl group."

(ix) FEATURE:
     (A) NAME/KEY: Modified-site
     (B) LOCATION: 30
     (D) OTHER INFORMATION: /label= Amide
         /note= "The carboxyl terminus is modified to an
         amide"

(xi) SEQUENCE DESCRIPTION: SEQ ID NO:35:

Gly Cys Gly His Arg Pro Leu Asp Lys Lys Arg Glu Glu Ala Pro Ser
1               5                   10                  15

Leu Arg Pro Ala Pro Pro Ile Ser Gly Gly Tyr Arg
            20              25              30

(2) INFORMATION FOR SEQ ID NO:36:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= Modified-Cys
            /note= "The thiol group of the amino terminal
            cysteine is protected by a 4-methoxybenzyl group;
            the thiol group of the other cysteine is protected
            by an acetamidomethyl group."

(xi) SEQUENCE DESCRIPTION: SEQ ID NO:36:

Cys Gly Cys Pro Leu Tyr Lys Lys Ile Ile Lys Lys Leu Leu Glu Ser
1               5                   10                  15

(2) INFORMATION FOR SEQ ID NO:37:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1..3
        (D) OTHER INFORMATION: /label= Modified-Cys
            /note= "The thiol group of each cysteine is
            protected with an acetamidomethyl group."

(ix) FEATURE:
        (A) NAME/KEY: Modified-site
        (B) LOCATION: 1..3
        (D) OTHER INFORMATION: /label= acetyl-Cys
            /note= "The amino terminal residue is
            linked to an acetyl group."

(xi) SEQUENCE DESCRIPTION: SEQ ID NO:37:

Cys Gly Cys Gln Ala Pro Leu Tyr Lys Lys Ile Ile Lys Lys Leu Leu
1               5                   10                  15

Glu Ser
```

TECHNETIUM-99M LABELED PEPTIDES FOR IMAGING INFLAMMATION

This application is a U.S. National Phase application claiming priority under 35 U.S.C. §§120 and 371 to International Application No. PCT/US94/02320, which is a continuation-in-part of U.S. Ser. No. 07/851,074, filed Mar. 12, 1992, now abandoned this application is also a continuation-in-part of U.S. Ser. No. 08/253,678, filed Jun. 3, 1994.

BACKGROUND OF THE INVENTION

1. Field of the Invention

This invention relates to radiodiagnostic agents and reagents for preparing such agents, and also methods for producing radiolabeled radiodiagnostic agents. Specifically, the invention relates to technetium-99m (Tc-99m) labeled agents, methods and kits for making such agents, and methods for using such agents to image sites of infection and inflammation in a mammalian body.

2. Description of the Prior Art

A variety of radionuclides are known to be useful for radioimaging, including $^{67}$Ga, $^{99m}$Tc (Tc-99m), $^{111}$In, $^{123}$I, $^{125}$I, $^{169}$Yb or $^{186}$Re. The sensitivity of imaging methods using radioactively-labeled peptides is much higher than other techniques known in the art, since the specific binding of the radioactive peptide concentrates the radioactive signal over the area of interest, for example, an inflammatory site.

There is a clinical need to be able to determine the location and/or extent of sites of focal or localized infection. In a substantial number of cases conventional methods of diagnosis (such as physical examination, x-ray, CT and ultrasonography) fail to identify such sites (e.g., an abscess). In some cases, biopsy may be resorted to, but is preferably avoided at least until it is necessary in order to identify the pathogen responsible for an abscess at a known location. Identifying the site of such "occult" infection is important because rapid localization of the problem is critical to effective therapeutic intervention.

In the field of nuclear medicine, certain pathological conditions can be localized or the extent of such conditions determined by imaging the internal distribution of administered radioactively-labeled tracer compounds (i.e. radiotracers or radiopharmaceuticals) that accumulate specifically at the pathological site. However, an abscess may be caused by any one of many possible pathogens, so that a radiotracer specific for a particular pathogen would have limited scope. On the other hand, infection is almost invariably accompanied by inflammation, which is a general response of the body to tissue injury. Therefore, a radiotracer specific for sites of inflammation would be expected to be useful in localizing sites of infection caused by any pathogen.

One of the main phenomena associated with inflammation is the location of leukocytes (white blood cells), usually monocytes and neutrophils, at the site of inflammation. A radiotracer specific for leukocytes would be useful in detecting leukocytes at the site of a localized infection. Currently approved nuclear medicine procedures for imaging sites of infection use either indium-111 labeled leukocytes ($^{111}$In-WBC) (see, e.g. Peters, 1992, J. Nucl. Med. 33: 65–67) or gallium-67 ($^{67}$Ga) citrate (see, e.g. Ebright et al., 1982, Arch. Int. Med. 142: 246–254).

A major disadvantage of using $^{111}$In-labeled WBCs is that the preparation of the radiotracer requires sterile removal of autologous blood, sterile isolation of the leukocytes from the blood, sterile labeling of the leukocytes using conditions that do not damage the cells (since damaged WBC are taken up by the reticuloendothelial system when re-injected) and return (re-injection) of the (now labeled) leukocytes to the patient. Furthermore, a delay of 12 to 48 hours between injection and imaging may be required for optimal images. While Tc-99m labeled leukocytes have been used to shorten this delay period (see, e.g. Vorne et al., 1989, J. Nucl. Med. 30: 1332–1336), ex-corporeal labeling is still required. A preferred radiotracer would be one that does not require removal and manipulation of autologous blood components.

$^{67}$Ga-citrate can be administered by intravenous injection. However, this compound is not specific for sites of infection or inflammation. Moreover, a delay of up to 72 hours is often required between injection of the radiotracer and imaging. In addition, the γ-(gamma) emission energies of $^{67}$Ga are not well suited to conventional gamma cameras.

Radiolabeled monoclonal and polyclonal antibodies raised against human leukocytes (including monocytes, neutrophils, granulocytes and other) have been developed. Tc-99m labeled antigranulocyte monoclonal antibodies (see, e.g. Lind et al., 1990, J. Nucl. Med. 31: 417–473) and $^{111}$In-labeled non-specific human immunoglobulin (see, e.g. LaMuraglia et al., 1989, J. Vasc. Surg. 10: 20–28) have been tested for the detection of inflammation secondary to infection. $^{111}$In-labeled IgG shares the disadvantages of $^{111}$In-labeled WBC, in that 24–48 hours are required between injection and optimal imaging. In addition, all radiolabeled antibodies are difficult to produce and face protracted regulatory agency approval procedures as biologics.

Small readily synthesized molecules are preferred for routinely used radiopharmaceuticals. There is clearly a need for small synthetic molecules that can be directly injected into a patient and will image sites of infection and inflammation by localizing at sites where leukocytes have accumulated.

One class of compounds known to bind to leukocytes are chemotactic peptides that cause leukocytes to move up a peptide concentration gradient (see Wilkinson, 1988, Meth. Enzymol. 162: 127–132). These compounds bind to receptors on the surface of leukocytes with very high affinity. These peptides are derived from a number of sources, including complement factors, bacteria, tuftsin, elastin, fibrinopeptide B, fibrinogen Bβ, platelet factor 4 and others. Small synthetic peptides derived from these chemotactic compounds and radiolabeled would be very useful as radiotracers for imaging sites of inflammation in vivo.

Radiolabeled peptides have been reported in the prior art.

U.S. Pat. No. 4,986,979 relates to the use of radiolabeled chemotactic formyl peptides to radiolabel leukocytes ex-corporeally via a photoaffinity label.

EPC 90108734.6 relates to chemotactic formyl peptide—$^{111}$In-labeled DTPA conjugates.

PCT WO90/10463 relates to the use of radiolabeled chemotactic formyl peptides to radiolabel leukocytes ex-corporeally via a photoaffinity label.

Zoghbi et al., 1981, J. Nucl. Med. 22: 32 (Abst) disclose formyl peptide chemotactic factors derived from bacteria coupled to $^{111}$In-labeled transferrin.

Jiang et al., 1982, Nuklearmedizin 21: 110–113 disclose a chemotactic formylated peptide radiolabeled with $^{125}$I.

Fischman et al., 1991, J. Nucl. Med. 32: 482–491 relates to chemotactic formyl peptide—$^{111}$In-labeled DTPA conjugates.

The use of chelating agents for radiolabeling polypeptides, methods for labeling peptides and polypeptides with Tc-99m are known in the prior art and are disclosed in co-pending U.S. patent applications Ser. Nos. 07/653,012, now abandoned, which issued as U.S. Pat. No. 5,811,394; 07/807,062, which issued as U.S. Pat. No. 5,443,815; 07/871,282, a divisional of which issued as U.S. Pat. No. 5,720,934; and 07/893,981, which issued as U.S. Pat. No. 5,508,020, which are hereby incorporated by reference.

SUMMARY OF THE INVENTION

The present invention provides scintigraphic imaging agents that are peptide reagents radioactively-labeled with Tc-99m. The peptide reagents of the invention are comprised of specific binding peptides that bind leukocytes, covalently linked to a Tc-99m radiolabel binding moiety.

A first aspect of the invention comprises reagents for preparing scintigraphic imaging agents for imaging sites of inflammation within a mammalian body, said reagents comprising a leukocyte binding peptide having an amino acid sequence comprising between 3 and 100 amino acids and a Tc-99m radiolabel-binding moiety.

In a second aspect, the invention comprises a Tc-99m radiolabel binding moiety which forms a Tc-99m complex having a net charge of [−1].

In yet another aspect, the radiolabeled peptide reagents of the invention comprise a specific binding peptide that binds to leukocytes, and a Tc-99m radiolabel-binding moiety of formula

Cp(aa)Cp        I.

wherein Cp is a protected cysteine residue and (aa) stands for an amino acid, and wherein the radiolabel-binding moiety is covalently linked to the specific binding peptide. In a preferred embodiment, the amino acid is glycine. In another preferred embodiment, the radiolabel-binding moiety is linked to the specific peptide via one or more amino acids.

In another aspect, the invention provides peptide reagents comprising a Tc-99m radiolabel-binding moiety comprising a single thiol moiety having the following structure:

A—CZ(B)—[C(R$^1$R$^2$)]$_n$—X        II.

wherein A is H, HOOC, H$_2$NOC, (peptide)-NHOC, (peptide)-OOC or R$^4$; B is H, SH or —NHR$^3$, —N(R$^3$)-(peptide) or R$^4$; Z is H or R$^4$; X is SH or —NHR$^3$, —N(R$^3$)-(peptide) or R$^4$; R$^1$, R$^2$, R$^3$ and R$^4$ are independently H or straight or branched chain or cyclic lower alkyl; n is 0, 1 or 2; and: (1) where B is —NHR$^3$ or —N(R$^3$)-(peptide), X is SH and n is 1 or 2; (2) where X is —NHR$^3$ or —N(R$^3$)-(peptide), B is SH and n is 1 or 2; (3) where B is H or R$^4$, A is HOOC, H$_2$NOC, (peptide)-NHOC or (peptide)-OOC, X is SH and n is 0 or 1; (4) where A is H or R$^4$, then where B is SH, X is —NHR$^3$ or —N(R$^3$)-(peptide) and where X is SH, B is —NHR$^3$ or —N(R$^3$)-(peptide); (5) where X is H or R$^4$, A is HOOC, H$_2$NOC, (peptide)-NHOC or (peptide)-OOC and B is SH; (6) where Z is methyl, X is methyl, A is HOOC, H$_2$NOC, (peptide)-NHOC or (peptide)-OOC and B is SH and n is 0; and wherein the thiol moiety is in the reduced form.

Another aspect of the invention provides reagents for preparing scintigraphic imaging agents for imaging sites of inflammation within a mammalian body, the reagents comprising a leukocyte-binding peptide having an amino acid sequence comprising between 3 and 100 amino acids and a Tc-99m radiolabel-binding moiety that forms a Tc-99m complex that is electrochemically neutral.

In yet another aspect, the present invention provides reagents comprising leukocyte-binding peptides covalently linked to a Tc-99m radiolabel-binding moiety having the following structure:

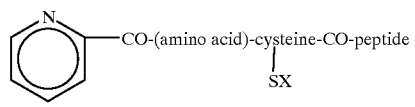

III.

[for purposes of this invention, radiolabel-binding moieties having this structure will be referred to as picolinic acid (Pic)-based moieties]; or

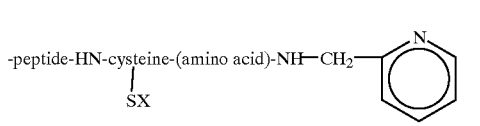

IV.

[for purposes of this invention, radiolabel-binding moieties having this structure will be referred to as picolylamine (Pica)-based moieties]; wherein X is H or a protecting group; (amino acid) is any amino acid; the Tc-99m radiolabel-binding moiety is covalently linked to the peptide, and the complex of the radiolabel-binding moiety and Tc-99m is electrically neutral. In a preferred embodiment, the amino acid is glycine and X is an acetamidomethyl protecting group. In additional preferred embodiments, the peptide is covalently linked to the Tc-99m radiolabel-binding moiety via an amino acid, most preferably glycine.

In yet another embodiment of the invention, reagents are provided for preparing scintigraphic imaging agents for imaging sites within a mammalian body, comprising a specific binding peptide and a bisamino bisthiol Tc-99m radiolabel-binding moiety covalently lined to the peptide. The bisamino bisthiol Tc-99m radiolabel-binding moiety in this embodiment of the invention has a formula selected from the group consisting of:

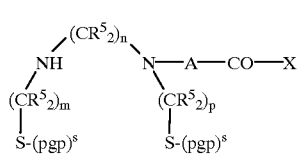

V.

wherein each R$^5$ can be independently H, CH$_3$ or C$_2$H$_5$; each (pgp)$^s$ can be independently a thiol protecting group or H; m, n and p are independently 2 or 3; A is linear or cyclic lower alkyl, aryl, heterocyclyl, combinations or substituted derivatives thereof; and X is a peptide;

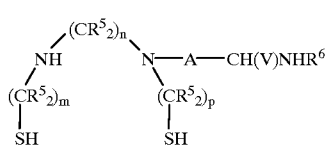

VI.

wherein each R$^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or CO-peptide; $R^6$ is H or a peptide; provided that when V is H, $R^6$ is a peptide and when $R^6$ is H, V is a peptide. [For purposes of this invention, radiolabel-binding moieties having these structures will be referred to as "BAT" moieties]. In one preferred embodiment, the peptide is covalently linked to the Tc-99m radiolabel-binding moiety via an amino acid, most preferably glycine.

The specific binding peptides of the invention may also be covalently linked to a polyvalent linking moiety. Polyvalent linking moieties of the invention are comprised of at least 2 identical linker functional groups capable of covalently bonding to specific binding peptides or Tc-99m binding moieties. Preferred linker functional groups are primary or secondary amines, hydroxyl groups, carboxylic acid groups or thiol-reactive groups. In preferred embodiments, the polyvalent linking moieties are comprised of bis-succinimdylmethylether (BSME), 4-(2,2-dimethylacetyl) benzoic acid (DMAB) and tris(succinimidylethyl)amine (TSEA).

The invention comprises scintigraphic imaging agents that are complexes between the reagents of the invention and Tc-99m, and methods for radiolabeling the reagents of the invention with Tc-99m. Radiolabeled complexes provided by the invention are formed by reacting the reagents of the invention with Tc-99m in the presence of a reducing agent. Preferred reducing agents include but are not limited to dithionite ion, stannous ion and ferrous ion. Complexes of the invention are also formed by labeling the reagents of the invention with Tc-99m by ligand exchange of a prereduced Tc-99m complex as provided herein.

The invention also provides kits for preparing scintigraphic imaging agents that are the reagents of the invention radiolabeled with Tc-99m. Kits for labeling the reagents provided by the invention with Tc-99m are comprised of a sealed vial containing a predetermined quantity of a reagent of the invention and a sufficient amount of reducing agent to label the reagent with Tc-99m.

This invention provides methods for preparing peptide reagents of the invention by chemical synthesis in vitro. In a preferred embodiment, peptides are synthesized by solid phase peptide synthesis.

This invention provides methods for using scintigraphic imaging agents that are Tc-99m labeled reagents for imaging sites of inflammation within a mammalian body by obtaining in vivo gamma scintigraphic images. These methods comprise administering an effective diagnostic amount of Tc-99m labeled reagents of the invention and detecting the gamma radiation emitted by the Tc-99m label localized at the site of inflammation within the mammalian body.

Specific preferred embodiments of the present invention will become evident from the following more detailed description of certain preferred embodiments and the claims.

DETAILED DESCRIPTION OF THE INVENTION

Figure 1:
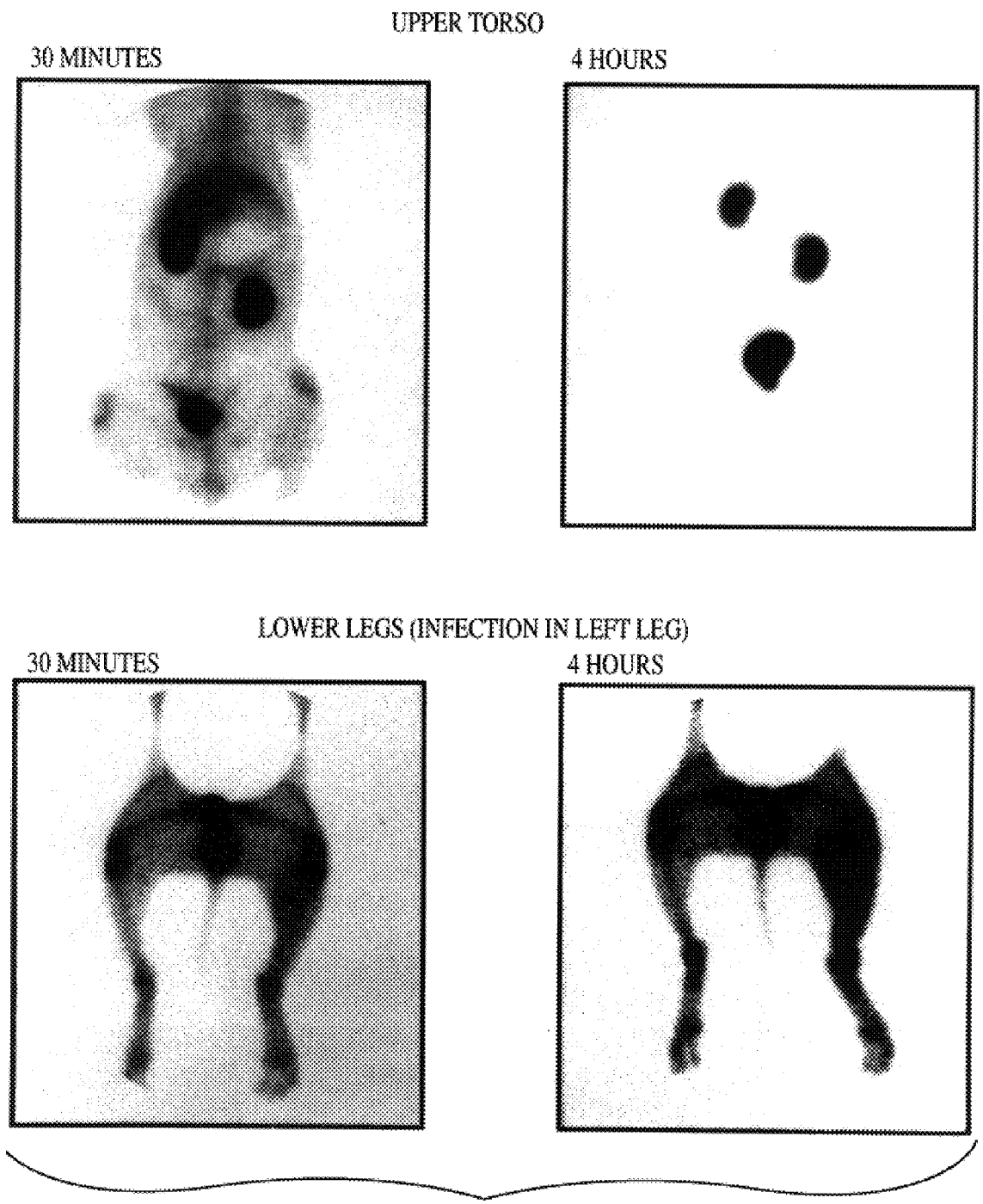
FIG. 1 illustrates a gamma-scintiphoto of a New Zealand white rabbit treated as described in Example 3.

The present invention provides reagents for preparing Tc-99m radiolabeled scintigraphic imaging agents for imaging target sites within a mammalian body. The reagents comprise a specific binding peptide that binds to leukocytes, covalently linked to a Tc-99m radiolabel complexing group.

The peptides of this invention bind to leukocytes, preferably monocytes and neutrophils and most preferably to neutrophils. For purposes of this invention, the term "bind to leukocytes" is intended to mean that the peptides of the present invention are capable of accumulating at sites of infection or inflammation in mammalian body sufficient to allow detection of such sites by gamma scintigraphy.

In Cp(aa)Cp-containing peptides, the Cp is a protected cysteine where the S-protecting groups are the same or different and may be but not limited to:

—$CH_2$-aryl (aryl is phenyl or alkyl or alkyloxy substituted phenyl);

—CH-(aryl)$_2$, (aryl is phenyl or alkyl or alkyloxy substituted phenyl);

—C-(aryl)$_3$, (aryl is phenyl or alkyl or alkyloxy substituted phenyl);

—$CH_2$-(4-methoxyphenyl);

—CH-(4-pyridyl)(phenyl)$_2$;

—C(CH$_3$)$_3$

—9-phenylfluorenyl;

—$CH_2$NHCOR (R is unsubstituted or substituted alkyl or aryl);

—$CH_2$—NHCOOR (R is unsubstituted or substituted alkyl or aryl);

—CONHR (R is unsubstituted or substituted alkyl or aryl);

—$CH_2$—S—$CH_2$-phenyl

The preferred protecting group has the formula —$CH_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl. labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides known in the prior art have effective half-lives which are much longer (for example, $^{111}$In, which has a half-life of 67.4 h) or are toxic (for example, $^{125}$I).

Each specific-binding peptide-containing embodiment of the invention is comprised of a sequence of amino acids. Particular amino acids comprising the peptides of this invention may be L- or D-amino acids, naturally occurring and otherwise; D-amino acids are indicated by a subscript D. Reagents provided by the invention include but are not limited to the following compounds:

---

Leukocyte Binding Peptides formyl.MLFC$_{Acm}$GC$_{Acm}$ (SEQ. ID NO. 1)
C$_{Acm}$GC$_{Acm}$(VGVAPG)$_3$ (SEQ. ID NO. 2)
formyl.MILFC$_{Acm}$GC$_{Acm}$ (SEQ. ID NO. 3)
C$_{Acm}$GC$_{Acm}$TKPR (SEQ. ID NO. 4)

-continued

Leukocyte Binding Peptides formyl.MLFC$_{Acm}$G.Pica (SEQ. ID NO. 5)
formyl.Nle.LF.Nle.YKC$_{Acm}$GC$_{Acm}$ (SEQ. ID NO. 6)
Pic.GC$_{Acm}$(VGVAPG)$_3$amide (SEQ. ID NO. 7)
Pic.GC$_{Acm}$(VPGVG)$_4$amide (SEQ. ID NO. 8)
Pic.GC$_{Acm}$PLYKKIIKKLLES (SEQ. ID NO. 9)
C$_{Acm}$GC$_{Acm}$GGPLYKKIIKKLLES (SEQ. ID NO. 10)
pGlu.GVNDNEEGFFSARC$_{Acm}$GC$_{Acm}$amide (SEQ. ID NO. 11)
(VPGVG)$_4$GGGC$_{Acm}$GC$_{Acm}$amide (SEQ. ID NO. 12)
(VGVAPG)$_3$GGGC$_{Acm}$GC$_{Acm}$amide (SEQ. ID NO. 13)
acetyl.C$_{Acm}$GC$_{Acm}$GGG(VPGVG)$_4$amide (SEQ. ID NO. 14)
acetyl.C$_{Acm}$GC$_{Acm}$.Aca.(VPGVG)$_4$amide (SEQ. ID NO. 15)
(acetyl.CC$_{Acm}$GC$_{Acm}$PLYKKIIKKLLES)$_2$.BSME (SEQ. ID NO. 16)
acetyl.CGGGPLYKKIIKKLLES (SEQ. ID NO. 16)
Pic.GC(VGVAPG)$_3$amide (SEQ. ID NO. 17)
pGlu.GVNDNEEGFFSARGGCamide (SEQ. ID NO. 18)
acetyl.(LKKL)$_5$C$_{Acm}$GC$_{Acm}$amide (SEQ. ID NO. 19)
[BAT].GGPLYKKIIKKLLES (SEQ. ID NO. 20)
formyl.MLFK.[BAT].amide (SEQ. ID NO. 21)
formyl.Thp.LF.[BAM]
formyl.MLFK.[BAM] (SEQ. ID NO. 22)
[BAT].(VPGVG)$_4$amide (SEQ. ID NO. 23)
formyl.MLFK.[BAT].KKKKKamide (SEQ. ID NO. 24)
formyl.MLFK.[BAT].GSGSamide (SEQ. ID NO. 25)
formyl.MLFK.[BAT].E (SEQ. ID NO. 26)
formyl.MLFK.[BAT].EGE (SEQ. ID NO. 27)
formyl.M.DpgF.[BAM] (SEQ. ID NO. 28)
[BAT].(VGVAPG)$_3$amide
[DTPA].C$_{Acm}$GC$_{Acm}$PLYKKIIKKLLES (SEQ. ID NO. 29)
[BAT].KKLLKKLYKKIIKKLLES (SEQ. ID NO. 30)
acetyl.CKKC$_{Acm}$GC$_{Acm}$PLYKKIIKKLLES (SEQ. ID NO. 31)
(acetylCGC$_{Acm}$GC$_{Acm}$GGPLYKKIIKKLLES)$_2$.BSME
formyl.MLF(NHCH$_2$CH$_2$OCH$_2$CH$_2$OCH$_2$CH$_2$NH)Pic.GC$_{Mob}$ (SEQ. ID NO. 32)
(acetyl.CKKC$_{Acm}$GC$_{Acm}$PLYKKIIKKLLES)$_2$BSME (SEQ. ID NO. 33)
[BAT].GHRPLDKKREEAPSLRPAPPPISGGGYRamide (SEQ. ID NO. 34)
acetyl.KKKKKC$_{Acm}$GC$_{Acm}$GGPLYKKIIKKLLES
(formyl.MLFK.[BAT].GGC$_{Acm}$GC$_{Acm}$GGC.amide)$_2$.BSME
Pic.GC$_{Acm}$GHRPLDKKREEAPSLRPAPPPISGGGYRamide (SEQ. ID NO. 35)
(formylMLFKGGC$_{Acm}$GC$_{Acm}$GGCamide)$_2$.BSME

[Single-letter abbreviations for amino acids can be found in G. Zubay, Biochemistry (2d. ed.), 1988 (MacMillen Publishing: New York) p. 33; Dgp = dipropylglycine; pGlu = pyro-glutamic acid; Nle = norleucine; Acm = acetamidomethyl; Mob = 4-Methoxybenzyl; Aca = ε-aminocaproic acid; Pic = picolinic acid; Pica = picolylamine (2-(aminomethyl)pyridine); [BAT] = $N^6,N^9$-bis(2-methyl-2-mercaptopropyl)-6,9-diazanonanoic acid; Thp = 4-aminotetrahydrothiopyran-4-carboxylic acid; [BAM] = $N^6,N^9$-bis(2-methyl-2-mercaptopropyl)-1,6,9-triazanonanoic acid; BSME = bis-succinimidylmethylether; DTPA = diethylenetriamine pentaacetic acid; peptides are linked to BSME linkers via the free thiol moiety of the unprotected cysteine residue (C) in each such peptide).

Peptides of the present invention can be chemically synthesized in vitro. Peptides of the present invention can generally advantageously be prepared on an amino acid synthesizer. The peptides of this invention can be synthesized wherein the complexing group is covalently lined to the peptide during chemical in vitro synthesis, using techniques well known to those with skill in the art. Such peptides covalently-linked to the complexing group upon synthesis are advantageous because specific sites of covalent linkage can be determined therein.

Radiolabel binding moieties of the invention may be introduced into the target specific peptide during peptide synthesis. For embodiments comprising picolinic acid [(Pic-); e.g., Pic-Gly-Cys(protecting group)-], the radiolabel-binding moiety can be synthesized as the last (i.e., amino-terminal) residue in the synthesis. In addition, the picolinic acid-containing radiolabel-binding moiety may be covalently linked to the ε-amino group of lysine to give, for example, αN(Fmoc)-Lys-εN[Pic-Gly-Cys(protecting group)], which may be incorporated at any position in the peptide chain. This sequence is particularly advantageous as it affords an easy mode of incorporation into the target binding peptide.

Similarly, the picolylamine (Pica)-containing radiolabel-binding moiety [-Cys(protecting group)-Gly-Pica] can be prepared during peptide synthesis by including the sequence [-Cys(protecting group)-Gly-] at the carboxyl terminus of the peptide chain. Following cleavage of the peptide from the resin the carboxyl terminus of the peptide is activated and coupled to picolylamine. This synthetic route requires that reactive side-chain functionalities remain masked (protected) and do not react during the conjugation of the picolylamine.

Examples of small synthetic peptides containing the Pic-Gly-Cys- and -Cys-Gly-Pica chelators are provided in the Examples hereinbelow. This invention provides for the incorporation of these chelators into virtually any peptide capable of specifically binding to leukocytes in vivo, resulting in a radiolabeled peptide having Tc-99m held as neutral complex.

This invention also provides specific-binding small synthetic peptides which incorporate bisamine bisthiol (BAT or BAM) chelators which may be labeled with Tc-99m. This invention provides for the incorporation of these chelators into virtually any peptide capable of specifically binding to leukocytes in vivo, resulting in a radiolabeled peptide having Tc-99m held as neutral complex. An examples of a small synthetic peptide containing a BAT chelator as radiolabel-binding moiety is provided in the Examples hereinbelow.

The specific binding peptides of the invention may also be covalently linked to a polyvalent linking moiety. Polyvalent linking moieties provided by the invention are comprised of at least 2 linker functional groups capable of covalently bonding to leukocyte-specific moieties, including linear and cyclic peptides. Such functional groups include but are not limited to primary and secondary amines, hydroxyl groups, carboxylic acid groups and thiol reactive groups. Polyvalent linking moieties are comprised of preferably at least three functional groups capable of being covalently linked to leukocyte-specific moieties, including linear and cyclic peptides. Preferred polyvalent lining moieties include amino acids such as lysine, homolysine, ornithine, aspartic acid and glutamic acid; linear and cyclic amines and polyamines; polycarboxylic acids; activated thiols; and thiol-reactive reagents such as di- and tri-maleimides. Also preferred are embodiments wherein the polyvalent linking moieties comprise a multiplicity of polyvalent linking moieties covalently linked to form a branched polyvalent linking moiety. Most preferred polyvalent linking moieties include bis-succinimidylmethylether, tris(succinimidylethyl)amine, 4-(2,2-dimethylacetyl)benzoic acid (DMAB) and derivatives thereof.

In forming a complex of radioactive technetium with the reagents of this invention, the technetium complex, preferably a salt of Tc-99m pertechnetate, is reacted with the reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a reagent of the invention to be labeled and a sufficient amount of reducing agent to label the reagent with Tc-99m. Alternatively, the complex may be formed by reacting a reagent of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts.

The reaction of the peptides of this invention with Tc-pertechnetate or preformed Tc-99m labile complex can be carried out in an aqueous medium at room temperature. When an anionic complex having a charge of [−1] is formed in the aqueous medium in the form of a salt with a suitable cation such as sodium cation, ammonium cation, mono, di- or tri-lower alkyl amine cation, etc. Any conventional salt of the anionic complex with a pharmaceutically acceptable cation can be used in accordance with this invention.

In a preferred embodiment of the invention, a kit for preparing technetium-labeled peptides is provided. The peptides of the invention can be chemically synthesized using methods and means well-known to those with skill in the art and described hereinbelow. Peptides thus prepared are comprised of between 3 and 100 amino acid residues, and are covalently linked to a radioisotope complexing group wherein the complexing group binds a radioisotope. An appropriate amount of the peptide is introduced into a vial containing a reducing agent, such as stannous chloride, in an amount sufficient to label the peptide with Tc-99m. An appropriate amount of a transfer ligand as described (such as tartrate, citrate, gluconate or mannitol, for example) can also be included. Technetium-labeled peptides according to the present invention can be prepared by the addition of an appropriate amount of Tc-99m or Tc-99m complex into the vials and reaction under conditions described in Example 2 hereinbelow.

Radioactively labeled peptides provided by the present invention are provided having a suitable amount of radioactivity. In forming the Tc-99m radioactive anionic complexes, it is generally preferred to form radioactive complexes in solutions containing radioactivity at concentrations of from about 0.01 millicurie (mCi) to 100 mCi per ml.

Technetium-labeled peptides provided by the present invention can be used for visualizing sites of inflammation, including abscesses and sites of "occult" infection. The Tc-99m labeled peptides provided by the present invention can also be used for visualizing sites of inflammation caused by tissue ischemia, including such disorders as inflammatory bowel disease and arthritis. In accordance with this invention, the technetium-labeled peptides or anionic complexes either as a complex or as a salt with a pharmaceutically acceptable cation are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 ml to about 10 ml. After intravenous administration, imaging of the organ or tumor in vivo can take place in a matter of a few minutes. However, imaging can take place, if desired, in hours or even longer, after injecting into patients. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The technetium-labeled peptides and complexes provided by the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole. (HBTU/HOBT), and using p-hydroxymethylphenoxy-methylpolystyrene (HMP) resin for carboxyl-terminus acids or Rink amide resin for carboxyl-terminus amides. Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature. Where appropriate, N-α-formyl groups were introduced either by treating the free N-terminus of a peptide bound to the resin with formic anhydride in dichloromethane at 0° C. for 2 h or by treating the cleaved, deprotected peptide with acetic anhydride in 98% formic acid. Where appropriate, N-α-acetyl groups were introduced by treating the free N-terminal amino group of the peptide bound to the resin with 20% (v/v) acetic anhydride in NMP for 30 min. Where appropriate the "Pica" group was introduced by conjugating picolylamine to a precursor peptide using diisopropylcarbodiimide and N-hydroxysuccinimide. Where appropriate, N-terminal [BAT] groups were introduced by treating free N-terminal amino groups of the peptide with $N^6,N^9$-bis(2-methyl-2-triphenylmethylthiopropyl)-$N^6$-(t-butoxycarbonyl)-6,9-diazanonanoic acid N-hydroxysuccinimide ester.

Where appropriate, BSME adducts were prepared by reacting single thiol-containing peptides (5 to 50 mg/mL in 50 mM sodium phosphate buffer, pH 8) with 0.5 molar equivalents of BMME (bis-maleimidomethylether) pre-dissolved in acetonitrile at room temperature for approximately 1 to 18 hours. The solution was concentrated and the product was purified by HPLC.

Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS) or by electrospray mass spectroscopy (ESMS).

EXAMPLE 2

A General Method for Radiolabeling with Tc-99m 0.1 mg of a peptide prepared as in Example 1 was dissolved in 0.1 mL of 0.05M potassium phosphate buffer (pH 7.4). Tc-99m gluceptate was prepared by reconstituting a Glucoscan vial (E.I. DuPont de Nemours, Inc.) with 1.0 mL of Tc-99m sodium pertechnetate containing up to 200 mCi and allowed to stand for 15 minutes at room temperature. 25 μl of Tc-99m gluceptate was then added to the peptide and the reaction allowed to proceed at room temperature or at 100° C. for 15 to 30 min and then filtered through a 0.2 μm filter.

The Tc-99m labeled peptide purity was determined by HPLC using a Vydak 218TP54 (RP-18, 5 micron, 220×4.6 mm) or Waters DeltaPak (RP-18, 5 micron, 150×3.9 mm) analytical column and eluted as described in the Footnotes in Table I. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 1 using the method described herein. Particular applications of the method are as follows: HPLC methods (indicated by superscript after $R_t$ in the Table below):

| | |
|---|---|
| Method 1: Brownlee column | 100% A to 100% $B_{70}$ in 10 min |
| Method 2: Vydak column | 100% A to 100% $B_{90}$ in 10 min |
| Method 3: Vydak column | 100% A to 100% $B_{70}$ in 10 min |
| Method 4: Waters column | 100% A to 100% $B_{90}$ in 10 min |
| Method 5: Waters column | 100% A to 100% $B_{90}$ in 20 min | wherein:

solvent A=0.1% $CF_3COOH/H_2O$ solvent $B_{70}$=0.1% $CF_3COOH/70\%$ $CH_3CN/H_2O$ solvent $B_{90}$=0.1% $CF_3COOH/90\%$ $CH_3CN/H_2O$ solvent flow rate=1 mL/min Vydak column=218TP54 RP-18, 5μ, 220 mm×4.6 mm analytical column Brownlee column=Spheri-5, RP-18 5μ, 220×4.6 mm column Waters column=DeltaPak RP-18, 5μ, 150 mm×3.9 mm analytical column

| Peptide Reagents | FABMS MH+ | Radiochemical Yield | HPLC $R_t$(min) |
|---|---|---|---|
| $C_{Mob}GC_{Acm}$PLYKKIIKKLLES | 2028 | 97% | Bound |
| formyl. MLFC$_{Acm}$GC$_{Acm}$ | 843 | 100% | 11.1, 11.9[1] |
| C$_{Acm}$GC$_{Acm}$(VGVAPG)$_3$amide | 1865 | 100% | 17.7[1] |
| formyl.MIFLC$_{Acm}$GC$_{Acm}$ | 957 | 100% | 11.4[1] |
| C$_{Acm}$GC$_{Acm}$TKPR | 906.5 | 100% | 16.1[1] |
| formyl.MLFC$_{Acm}$G. Pica | 760 | 100% | 10.9, 12.2[1] |
| formyl.Nle.LF.Nle.YKC$_{Acm}$GC$_{Acm}$ | 1230 | 97% | 15.6–16.8[2] |
| Pic.GC$_{Acm}$(VGVAPG)$_3$amide | 1795 | 92% | 12.4[2] |
| Pic.GC$_{Acm}$(VPGVG)$_4$amide | 1992 | 100% | 12.0[1] |
| Pic.GC$_{Acm}$PLYKKIIKKLLES | 1910 | 81% | 12.9, 13.3[3] |
| C$_{Acm}$GC$_{Acm}$GGPLYKKIIKKLLES | 2093 | 96% | 12.6[3] |
| pGlu.GVNDNEEGFFSARC$_{Acm}$GC$_{Acm}$amide | 1957 | 95% | 16.3, 16.7[3] |
| PicGC$_{Acm}$GHRPLDKKREEAPSLRPAPPPISGGYR | 3377 | 94% | 11.3[3] |
| (VPGVG)$_4$GGGC$_{Acm}$GC$_{Acm}$amide | 2231 | 67% | 11.2, 11.5[3] |
| (VGVAPG)$_3$GGGC$_{Acm}$GC$_{Acm}$amide | 2035 | 33% | 10.6[3] |
| Ac.C$_{Acm}$GC$_{Acm}$GGG(VPGVG)$_4$amide | 2275 | 97% | 9.6, 9.9[3] |
| Ac.C$_{Acm}$GC$_{Acm}$.Aca.(VPGVG)$_4$amide | 2216 | 76% | 11.6, 12.3[3] |
| Ac.CGGGPLYKKIIKKLLES | 1889 | 83% | 14.1–21.8[2] |
| Pic.GC(VGVAPG)$_3$amide | 1724 | 100% | 17.4[2] |
| pGlu.GVNDNEEGFFSARGGCamide | 1768* | 94% | 16.6, 12.4[2] |
| Ac.(LKKL)$_5$C$_{Acm}$GC$_{Acm}$amide | 2878 | 63% | 17.0–18.0[2] |
| [BAT]GGPLYKKIIKKLLES | 2006 | 94% | 9.5[4] |

-continued

| Peptide Reagents | FABMS MH⁺ | Radiochemical Yield | HPLC R$_t$(min) |
|---|---|---|---|
| [BAT]GHRPLDKKREEAPSLRPAPPPISGGGYRamide | 3357 | 93% | 10.4, 11.6² |
| formyl.MLFK.[BAT].amide | 884 | 99% | 12.6² |
| formyl.Thp.LF.[BAM] | 775** | 99% | 13.3, 13.6² |
| Ac.KKKKKC$_{Acm}$GC$_{Acm}$GGPLYKKIIKKLLES | 2776 | 98% | 10.2, 11.3⁴ |
| formyl.MLFK.[BAT] | 884 | 96% | 11.9, 13.7² |
| [BAT].(VPGVG)$_4$amide | 1974 | 96% | 11.9, 12.8⁴ |
| formyl.MLFK.[BAT].KKKKKamide | 1524 | 96% | 11.7, 12.2⁴ |
| formyl.MLFK.[BAT].GSGSamide | 1315 | 97% | 11.9, 12.8⁴ |
| formyl.MLFK.[BAT].E | 1013 | 99% | 12.3⁴ |
| formyl.M.Dpg.F.[BAM] | 1354 | 98% | 13.7⁴ |
| formyl.MLFK.[BAT].EGE | 1200 | 98% | 12.1⁴ |
| (formyl.MLFK.[BAT].GGC$_{Acm}$GC$_{Acm}$GGCamide)$_2$BSME | 3477 | 99% | 11.9, 12.4⁴ |
| (Ac.C$_{Acm}$GC$_{Acm}$PLYKKIIKKLLES)$_2$BSME | 4483 | 98% | 11.6⁴ |
| [DTPA]C$_{Acm}$GC$_{Acm}$PLYKKIIKKLLES | 2468 | 91% | 11.4–14.0⁴ |
| (Ac.CKKC$_{Acm}$GC$_{Acm}$PLYKKIIKKLLES)$_2$BSME | | | |
| (Ac.CGC$_{Acm}$GC$_{Acm}$GGPLYKKIIKKLLES)$_2$BSME | 4825* | 99% | 16.2⁴ |
| (formyl.MLFK.GC$_{Acm}$GC$_{Acm}$GGCamide)$_2$BSME | 2839* | | |
| [BAT].(VGVAPG)$_3$amide | 1778 | 98% | 11.4⁴ |
| Ac.C$_{Acm}$GC$_{Acm}$QAPLYKKIILKKLLES | 2220 | 100% | 16.6⁵ |
| [BAT].KKLLKKLYKKIIKKLLES | 2533 | 99% | Bound⁴ |

Ac = acetyl; other abbreviations as in "Leukocyte Binding Peptides" Table above
*ESMS data (M); **FABMS data (MNa⁺).

EXAMPLE 3

Scintigraphic Imaging and Biodistribution of Tc-99m Labeled Peptides

In order to demonstrate the effectiveness of Tc-99m labeled peptide reagents as provided above, New Zealand white rabbits were innoculated intramuscularly in the left calf with a potent strain of *E. coli*. After 24 h, the animals were sedated by i.m. injection of ketamine and xylazine, and then injected i.v. with Tc-99m labeled peptide ($\leq$150 µg, 2–10 mCi). The animals were positioned supine in the field of view of a gamma camera (LEAP colimator/photopeaked for Tc-99m) and imaged over the first hour post-injection, and then at approximately 1 h intervals over the next three hours post injection. Animals were allowed to recover between image acquisitions and re-anesthetized as needed.

Upon completion of the final imaging, each animal was sacrificed by overdose of phenobarbital i.v. and dissected to obtain samples of blood and of infected and control muscle tissue. The tissue samples were weighed, and along with a standard amount of the injected dose, were counted using a gamma counter, and the percent injected dose (per gram of tissue) remaining in the tissues was determined. Ratios of percent of injected dose per gram of infected versus non-infected muscle tissue, and of infected muscle tissue versus blood, were calculated for each peptide. These results are presented in the following Table. Scintiphotos of whole body and leg images of a rabbit injected with a Tc-99m labeled reagent of the invention, having the formula acetyl.KKKKKC$_{Acm}$GC$_{Acm}$GGPLYKKIIKKLLES(SEQ ID No.: 34)

are presented in FIG. 1.

| Peptide Reagents | Infected Muscle (% ID/g) | Control Muscle (% ID/g) | Ratio of Infected/ Control | Blood (% ID/g) | Ratio of Infected/ Blood |
|---|---|---|---|---|---|
| Ac.C$_{Acm}$GC$_{Acm}$GGG(VPGVG)$_4$amide | 0.0306 | 0.0077 | 3.97 | 0.049 | 0.63 |
| Ac.CGGGPLYKKIIKKLLES | 0.0235 | 0.0050 | 4.70 | 0.032 | 0.74 |
| formyl.MLFK.[BAT]amide | 0.0215 | 0.0028 | 7.68 | 0.006 | 3.58 |
| pGlu.GVNDNEEGFFSARC$_{Acm}$GC$_{Acm}$amide | 0.0165 | 0.0029 | 5.68 | 0.024 | 0.68 |
| formyl.M.Dpg.F.[BAM] | 0.0106 | 0.0007 | 15.14 | 0.003 | 3.53 |
| PicGC(VGVAPG)$_3$amide | 0.0106 | 0.0019 | 5.58 | 0.015 | 0.69 |
| (Ac.CC$_{Acm}$GC$_{Acm}$PLYKKIIKKLLES)$_2$BSME | 0.0082 | 0.0011 | 7.45 | 0.010 | 0.84 |
| C$_{Acm}$GC$_{Acm}$(VGVAPG)$_3$amide | 0.0067 | 0.0017 | 3.94 | 0.011 | 1.69 |
| C$_{Acm}$GC$_{Acm}$TKPR | 0.0060 | 0.0025 | 2.40 | 0.003 | 2.07 |
| Ac.KKKKKC$_{Acm}$GC$_{Acm}$GGPLYKKIIKKLLES | 0.0061 | 0.0019 | 5.60 | 0.006 | 0.93 |
| formyl.Thp.LF.[BAM] | 0.0048 | 0.0010 | 4.80 | 0.006 | 0.83 |
| [BAT].(VPGVG)$_4$amide | 0.0032 | 0.0006 | 5.33 | 0.002 | 1.68 |
| [BAT].GGPLYKKIIKKLLES | 0.0021 | 0.0003 | 7.00 | 0.004 | 0.50 |

(% ID/g) = percent injected dose per gram tissue; other abbreviations are as in the previous Tables.

It should be understood that the foregoing disclosure emphasizes certain specific embodiments of the invention and that all modifications or alternatives equivalent thereto are within the spirit and scope of the invention as set forth in the appended claims.

What is claimed is:

1. A reagent for preparing a scintigraphic imaging agent comprising a peptide that specifically binds to leukocytes, said peptide being covalently linked to a technetium-99m complexing moiety having a formula selected from the group consisting of:

Cp(aa)Cp    I.

wherein Cp is a protected cysteine and (aa) is any primary α- or β-amino acid not having a thiol-group containing sidechain;

a technetium-99m complexing moiety comprising a single thiol having a formula:

A—CZ(B)—[C(R¹R²)]ₙ—X    II.

wherein
A is H, HOOC, H₂NOC, (peptide)-NHOC, (peptide)-OOC or R⁴;
B is H, SH, —NHR³, —N(R³)-(peptide), or R⁴;
X is H, SH, —NHR³, —N(R³)-(peptide) or R⁴;
Z is H or R⁴;
R¹, R², R³ and R⁴ are independently H or lower straight or branched chain or cyclic alkyl;
n is 0, 1 or 2; and
where B is —NHR³ or —N(R³)-(peptide), X is SH, and n is 1 or 2;
where X is —NHR³ or —N(R³)-(peptide), B is SH, and n is 1 or 2;
where B is H or R⁴, A is HOOC, H₂NOC, (peptide)-NHOC or (peptide)-OOC, X is SH, and n is 0 or 1;
where A is H or R⁴, then where B is SH, X is —NHR³ or —N(R³)-(peptide) and
where X is SH, B is —NHR³ or —N(R³)-(peptide);
where X is H or R⁴, A is HOOC, H₂NOC, (peptide)-NHOC or (peptide)-OOC and B is SH;
where Z is methyl, X is methyl, A is HOOC, H₂NOC, (peptide)-NHOC or (peptide)-OOC, B is SH and n is 0;
and wherein the thiol moiety is in the reduced form;

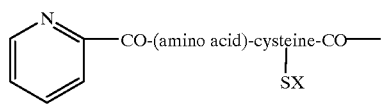    III.

wherein
X=H or a protecting group;
(amino acid)=any amino acid;

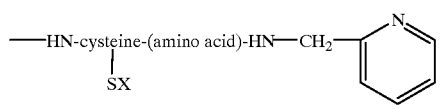    IV.

wherein
X=H or a protecting group;
(amino acid)=any amino acid;

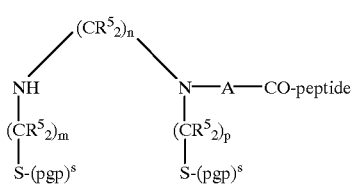    V.

wherein
each R⁵ is independently H, CH₃ or C₂H₅;
each (pgp)ˢ is independently a thiol protecting group or H;
m, n and p are independently 2 or 3;
A=linear lower alkyl, cyclic lower alkyl, aryl, heterocyclyl, or a combination thereof; and

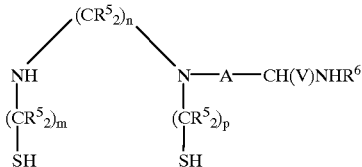    VI.

wherein
each R⁵ is independently H, lower alkyl having 1 to 6 carbon atoms, phenyl, or phenyl substituted with lower alkyl or lower alkoxy;
m, n and p are independently 1 or 2;
A=linear lower alkyl, cyclic lower alkyl, aryl, heterocyclyl, or a combination thereof;
V=H or —CO-peptide;
R⁶=H or peptide;
and wherein when V=H, R⁶=peptide and when R⁶=H, V=—CO-peptide.

2. The reagent of claim 1 wherein the peptide and the technetium-99m complexing moiety are covalently linked through one or more amino acids.

3. The reagent of claim 2 wherein the technetium-99m complexing moiety is Cp(aa)Cp and wherein Cp has a protecting group of the formula

—CH₂—NH—CO—R wherein R is lower alkyl having 1 to 6 carbon atoms, a 2-pyridyl, a 3-puridyl, a 4-pyridyl, a phenyl, or a phenyl substituted with a lower alkyl, a hydroxy, a lower alkoxy, a carboxy, or a lower alkoxycarbonyl.

4. The reagent of claim 1 wherein the technetium-99m complexing moiety is:

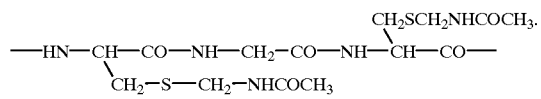

5. A scintigraphic imaging agent comprising the reagent of claim 1 radiolabeled with technetium-99m.

6. The reagent of claim 1 wherein the peptide is platelet factor 4.

7. The reagent of claim 1, wherein the peptide comprises an amino acid sequence selected from the group consisting of formylMLF and formyl.Nle.LF.Nle.

8. The reagent of claim 1, wherein the peptide is tuftsin.

9. The reagent of claim 1, wherein the peptide is selected from the group consisting of fibrinopeptide B and fibrinogen Bβ-chain.

10. The reagent of claim 1, having an amino acid sequence selected from the group consisting of:

C_{Mob}GC_{Acm}PLYKKIIKKLLES (SEQ ID No.: 36);
Pic.GC_{Acm}PLYKKIIKKLLES (SEQ ID No.: 9);
C_{Acm}GC_{Acm}GGPLYKKIIKKLLES (SEQ ID No.: 10);
acetyl.CGGGPLYKKIIKKLLES (SEQ ID No.: 16);
[BAT].GGPLYKKIIKKLLES (SEQ ID No.: 20);
[DTPA].C_{Acm}GC_{Acm}PLYKKIIKKLLES (SEQ ID No.: 29);
[BAT].KKLLKKLYKKIIKKLLES (SEQ ID No.: 30);
AC.C_{Acm}GC_{Acm}QAPLYKKIIKKLLES (SEQ ID No.: 37);

(Acetyl-NHCHCO-Cys(Acm)-Gly-Cys(Acm)-Pro-Leu-Tyr-Lys-Lys-Ile-Ile-Lys-Lys-Leu-Leu-Glu-Ser;

(Acetyl-NHCHCO-Gly-Cys(Acm)-Gly-Cys(Acm)-Gly-Gly-Pro-Leu-Tyr-Lys-Lys-Ile-Ile-Lys-Lys-Leu-Leu-Glu-Ser; and (Acetyl-Lys-Lys-NHCHCO-Cys(Acm)-Gly-Cys(Acm)-Pro-Leu-Tyr-Lys-Lys-Ile-Ile-Lys-Lys-Leu-Leu-Glu-Ser.

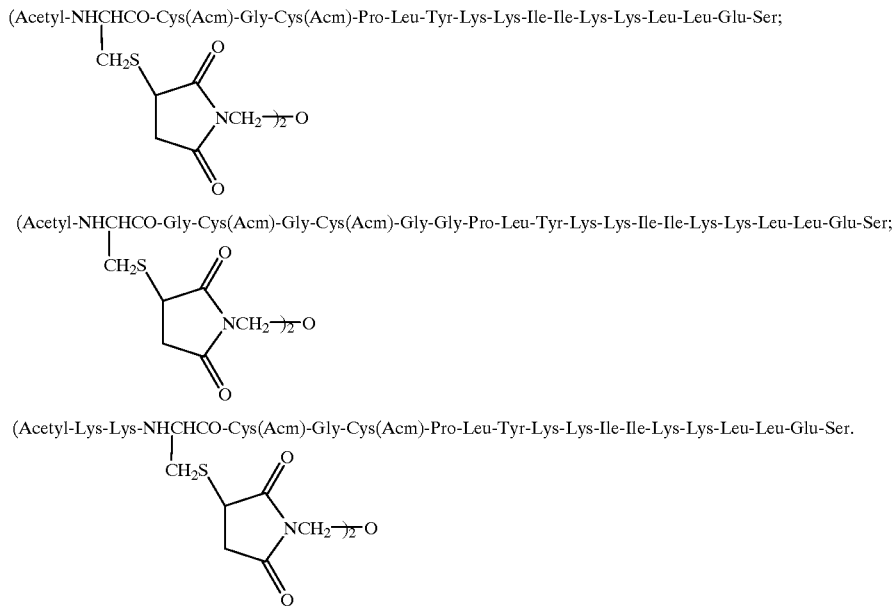

11. The reagent of claim 7, having an amino acid sequence selected from the group consisting of:

formyl.MLFC$_{Acm}$GC$_{Acm}$ (SEQ ID No.: 1);
formyl.MIFLC$_{Acm}$GC$_{Ac}$ (SEQ ID No.: 3);
formyl.MLFC$_{Acm}$GPica (SEQ ID No.: 5);
formyl.Nle.LF.Nle.YKC$_{Acm}$GC$_{Acm}$ (SEQ ID No.: 6);
formyl.MLFK.[BAT].amide (SEQ ID No.: 21);
formyl.Thp.LF.[BAM];
formyl.MLFK.[BAT] (SEQ ID No.: 22);
formyl.MLFK.[BAT].KKKKK.amide;
formyl.MLFK.[BAT].GSGS.amide;
formyl.MLFK.[BAT].E (SEQ ID No.: 25);
formyl.M.Dpg.F.[BAM] (SEQ ID No.: 26);
formyl.MLFK.[BAT].EGE;

C$_{Acm}$GC$_{Acm}$(VGVAPG)$_3$amide (SEQ ID No. 2);
Pic.GC$_{Acm}$(VGVAPG)$_3$amide (SEQ ID No. 7);
Pic.GC$_{Acm}$(VPGVG)$_4$amide (SEQ ID No. 8);
Pic.GC(VGVAPG)$_3$amide (SEQ ID No. 17);
[BAT].(VGVAPG)$_3$amide (SEQ ID No. 28); and
[BAT].(VPGVG)$_4$amide (SEQ ID No. 23).

13. The reagent of claim 9, having an amino acid sequence selected from the group consisting of:

pGlu.GVNDNEEGFFSARGGC.amide (SEQ ID No. 18);
Pic.GC$_{Acm}$GHRPLDKKREEAPSLRPAPPPISGGGYR (SEQ ID No. 35); and [BAT]. GHRPLDKKREEAPSL-RPAPPPISGGGYR.amide (SEQ ID No. 33).

(formyl-Met-Leu-Phe-Lys-Gly-Gly-Cys(Acm)-Gly-Cys-(Acm)-Gly-Gly-NHCHCO.NH$_2$

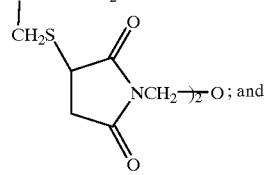; and (formyl-Met-Leu-Phe-NHCHCO-Gly-Gly-Cys(Acm)-Gly-Cys-(Acm)-Gly-Gly-NHCHCO.NH$_2$

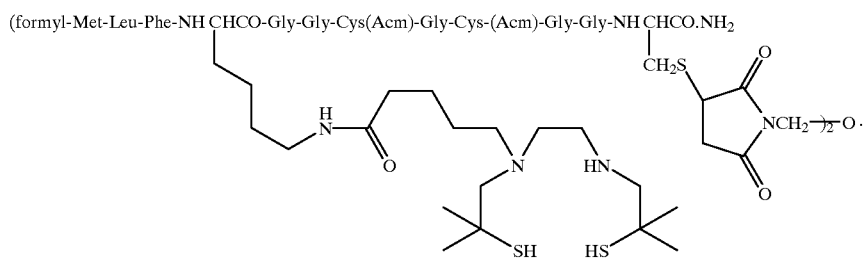

12. The reagent of claim 2, having an amino acid sequence selected from the group consisting of:

14. The reagent of claim 8, having a formula:
C$_{Acm}$GC$_{Acm}$TKPR (SEQ ID No.: 4).

15. A reagent comprising a) a multiplicity of synthetically prepared, leukocyte-binding peptides, each peptide comprising from three to 100 amino acids and being covalently linked to a polyvalent linker; and b) a technetium complexing moiety; wherein the technetium complexing moiety is covalently linked to a specific amino acid of each of a plurality of the peptides, the linker, or both.

16. The reagent of claim 15, wherein the linker is selected from the group consisting of bis-succinimidyl-methylether, 4-(2,2-dimethylacetyl)benzoic acid, tris(succinimidylethyl)amine, a derivative of bis-succinimidyl-methylether, and a derivative of 4-(2,2-dimethylacetyl)benzoic acid, tris(succinimidylethyl)amine.

17. A complex formed by reacting the reagent of claim 1 with technetium-99m in the presence of a reducing agent.

18. The complex of claim 17, wherein the reducing agent is selected from the group consisting of a dithionite ion, a stannous ion, and a ferrous ion.

19. A complex formed by labeling the reagent of claim 1 with technetium-99m by ligand exchange of a prereduced technetium-99m complex.

20. A kit for preparing a radiopharmaceutical preparation, said kit comprising a sealed vial containing a predetermined quantity of the reagent of claim 1 and a sufficient amount of a reducing agent to label the reagent with technetium-99m.

21. A method for imaging a site of inflammation within a mammalian body comprising the steps of a) administering an effective diagnostic amount of the scintigraphic imaging agent of claim 5; and b) detecting the Tc-99m localized at the site of inflammation.

22. A process for preparing the reagent according to claim 1, wherein the reagent is chemically synthesized in vitro.

23. The process of claim 22, wherein the peptide is synthesized by solid phase peptide synthesis.

24. The reagent of claim 1, wherein the technetium-99m complexing moiety is covalently linked to the peptide during solid phase peptide synthesis.

25. The reagent of claim 1, wherein the technetium-99m complexing moiety is covalently linked to the peptide during in vitro chemical synthesis.

26. A method for labeling a reagent according to claim 1, comprising the step of reacting the reagent with Tc-99m in the presence of a reducing agent.

27. The method of claim 26, wherein the reducing agent is selected from the group consisting of a dithionite ion, a stannous ion, and a ferrous ion.

28. A reagent for preparing a scintigraphic imaging agent comprising a peptide that specifically binds to leukocytes, covalently linked to a-technetium-99m complexing moiety comprising a single thiol containing moiety of formula:

A—CZ(B)—(C($R^1R^2$))$_n$—X    II.

wherein

A is H, HOOC, $H_2$NOC, (amino acid or peptide)-NHOC, (amino acid or peptide)-OOC or $R^4$ B is H, SH, —$NHR^3$,—$N(R^3)$-(amino acid or peptide), or $R^4$;

X is H, SH,—$NHR^3$,—$N(R^3)$-(amino acid or peptide or $R^4$;

Z is H or $R^4$ $R^1$, $R^2$, $R^3$ and $R^4$ are independently H or lower straight or branched chain or cyclic alkyl;

n is 0, 1 or 2; and
  where B is —$NHR^3$ or —$N(R^3)$-(amino acid or peptide), X is SH, and n is 1 or 2;
  where X is —$NHR^3$ or —$NHR^3$ or —$N(R^3)$-(amino acid or peptide), B is SH, and n is 1 or 2;
  where B is H or $R^4$, A is HOOC, $H_2$NOC, (amino acid or peptide)-NHOC or (amino acid or peptide)-OOC, X is SH, and n is 0 or 1;
  where A is H or $R^4$, then where B is SH, X is —$NHR^3$ or —$N(R^3)$-(amino acid peptide) and where X is SH, B is —$NHR^3$ or —$N(R^3)$-(amino acid or peptide);
  where X is H or $R^4$, A is HOOC, $H_2$NOC, (amino acid or peptide), _NHOC or (amino acid or peptide)-OOC and B is SH;
  where Z is methyl, X is methyl, A is HOOC, $H_2$NOC, (amino acid or peptide)-NHOC or (amino acid or peptide)-OOC, B is SH and n is 0;
  and wherein the thiol moiety is in the reduced form and (amino acid) is any primary α- or β-amino acid not containing a thiol group.

29. The reagent of claim 28, wherein the technetium-99m complexing moiety is selected from the group consisting of:

IIa. -(amino acid)$^1$-(amino acid)$^2$-{A—CZ(B)—(C($R^1R^2$))$_n$X},

IIb. -{A—CZ(B)—[C($R^1R^2$)]$_n$—X}—(amino acid)$^1$-(amino acid)$^2$,

IIc. -(a primary a, ω- or β, ω-diamino acid)-(amino acid)$^1$-{A—CZ (B)—{C($R^1R^2$))$_n$—X}, and IId. -{A—CZ(B)—(C($R^1R^2$)$_n$—X}-(amino acid)$^1$-(a primary α,ω- or β, ω-diamino acid), wherein (amino acid)$^1$ and (amino acid)$^2$ are each independently any naturally-occurring, modified, substituted or altered α- or β-amino acid not containing a thiol group.

30. A pharmaceutical composition for imaging a site of inflammation within a mammalian body comprising the scintigraphic imaging agent of claim 5 in a pharmaceutically acceptable carrier.

31. The method of claim 21, wherein the imaging agent is elastin.

* * * * *